US009827345B2

(12) United States Patent
Carvell et al.

(10) Patent No.: US 9,827,345 B2
(45) Date of Patent: Nov. 28, 2017

(54) METHODS AND COMPOSITIONS SUITABLE FOR IMPROVED REATTACHMENT OF DETACHED CARTILAGE TO SUBCHONDRAL BONE

(71) Applicant: Smith & Nephew, Inc., Memphis, TN (US)

(72) Inventors: Kelsey Jean Carvell, Malden, MA (US); Ruth Cheng, Natick, MA (US); Graham Smith, Newburyport, MA (US); Drew Burdon, North Yorkshire (GB)

(73) Assignee: Smith & Nephew, Inc., Memphis, TN (US)

( * ) Notice: Subject to any disclaimer, the term of this patent is extended or adjusted under 35 U.S.C. 154(b) by 704 days.

(21) Appl. No.: 14/075,146

(22) Filed: Nov. 8, 2013

(65) Prior Publication Data
US 2014/0170106 A1  Jun. 19, 2014

Related U.S. Application Data

(60) Provisional application No. 61/736,664, filed on Dec. 13, 2012, provisional application No. 61/723,990, filed on Nov. 8, 2012.

(51) Int. Cl.
A61L 24/10 (2006.01)
A61L 24/00 (2006.01)
A61L 27/22 (2006.01)
A61L 27/54 (2006.01)
A61K 9/00 (2006.01)
A61K 47/42 (2017.01)

(52) U.S. Cl.
CPC ......... A61L 24/0015 (2013.01); A61L 24/106 (2013.01); A61L 27/225 (2013.01); A61L 27/54 (2013.01); A61K 9/0024 (2013.01); A61K 47/42 (2013.01); A61L 2300/254 (2013.01); A61L 2300/426 (2013.01); A61L 2300/43 (2013.01); A61L 2300/63 (2013.01); A61L 2300/802 (2013.01); A61L 2430/06 (2013.01)

(58) Field of Classification Search
None
See application file for complete search history.

(56) References Cited

U.S. PATENT DOCUMENTS

| 4,542,025 | A | 9/1985 | Tice et al. |
|---|---|---|---|
| 4,827,911 | A | 5/1989 | Broadwin et al. |
| 4,842,578 | A | 6/1989 | Johnson et al. |
| 5,206,023 | A | 4/1993 | Hunziker |
| 5,433,215 | A | 7/1995 | Athanasiou et al. |
| 5,871,462 | A | 2/1999 | Yoder et al. |
| 5,906,934 | A | 5/1999 | Grande et al. |
| 5,944,686 | A | 8/1999 | Patterson et al. |
| 6,068,604 | A | 5/2000 | Krause et al. |
| 6,491,692 | B1 | 12/2002 | Meislin |
| 6,784,282 | B2 | 8/2004 | Hwang et al. |
| 7,575,743 | B2 | 8/2009 | Hunziker |
| 7,727,542 | B2 | 6/2010 | DiBenedetto et al. |
| 7,780,740 | B2 | 8/2010 | Steinberg |
| 2001/0037106 | A1 | 11/2001 | Shadduck |
| 2002/0091403 | A1 | 7/2002 | Bonutti |
| 2002/0116063 | A1 | 8/2002 | Giannetti et al. |
| 2002/0122790 | A1* | 9/2002 | Hunziker ............. C12N 5/0655 424/93.7 |
| 2003/0008826 | A1 | 1/2003 | Hwang et al. |
| 2003/0009166 | A1 | 1/2003 | Moutafis et al. |
| 2003/0040763 | A1 | 2/2003 | Moutafis et al. |
| 2003/0099630 | A1 | 5/2003 | DiBenedetto et al. |
| 2003/0114936 | A1 | 6/2003 | Sherwood et al. |
| 2003/0125660 | A1 | 7/2003 | Moutafis et al. |
| 2003/0125727 | A1 | 7/2003 | Truckai et al. |
| 2003/0207232 | A1* | 11/2003 | Todd ................... A61C 1/0092 433/88 |
| 2004/0033212 | A1 | 2/2004 | Thomson et al. |
| 2004/0092921 | A1 | 5/2004 | Kadziauskas et al. |
| 2004/0214322 | A1 | 10/2004 | Park et al. |
| 2005/0043814 | A1 | 2/2005 | Kusanagi et al. |
| 2006/0083728 | A1 | 4/2006 | Kusanagi et al. |
| 2006/0156875 | A1 | 7/2006 | McRury et al. |
| 2006/0229550 | A1 | 10/2006 | Staid et al. |
| 2007/0083120 | A1 | 4/2007 | Cain et al. |
| 2007/0088217 | A1 | 4/2007 | Babaev |

(Continued)

FOREIGN PATENT DOCUMENTS

CN 101352581 A 1/2009
EP 2389881 A1 11/2011

(Continued)

OTHER PUBLICATIONS

Goldring, Mary B. "Osteoarthritis and cartilage: the role of cytokines." Current rheumatology reports 2.6 (2000): 459-465.*
Patent Examination Report from related Australian Application No. 2013342255 dated Jun. 30, 2016.
Saw, et al., "Articular Cartilage Regeneration with Autologous Peripheral Blood Progenitor Cells and Hyaluronic Acid After Arthroscopic Subchondral Driling: A Report of 5 Cases with Histogy", The Journal of Arthroscopic and Related Surgeries; vol. 27, No. 4; Apr. 2011; pp. 493-605.
International Search Report dated Aug. 12, 2014 for PCT/US2013/069118, filed on Nov. 8, 2013, 13 pages.
International Preliminary Report on Patentability dated May 21, 2015 for PCT/US2013/069118, filed on Nov. 8, 2013, 10 pages.

(Continued)

Primary Examiner — John Pak
Assistant Examiner — Daniel Branson
(74) Attorney, Agent, or Firm — Burns & Levinson LLP; Joseph M. Maraia

(57) ABSTRACT

The methods and compositions disclosed herein are effective in the promoting the reattachment of delaminated cartilage to bone. The methods (and related compositions) comprise the removal of the acellular layer of the delaminated cartilage thereby exposing the underlying chondrocyte cells thereby allowing the promotion of the reattachment of the delaminated cartilage.

10 Claims, 3 Drawing Sheets

(56) References Cited

U.S. PATENT DOCUMENTS

| | | | |
|---|---|---|---|
| 2007/0098675 A1 | 5/2007 | Elisseeff et al. | |
| 2007/0179343 A1 | 8/2007 | Shelokov | |
| 2008/0044423 A1 | 2/2008 | Cochrane et al. | |
| 2008/0199513 A1 | 8/2008 | Beretta | |
| 2008/0311190 A1 | 12/2008 | Chtourou | |
| 2009/0047322 A1 | 2/2009 | Vange et al. | |
| 2009/0155378 A1 | 6/2009 | Behnam et al. | |
| 2009/0221076 A1 | 9/2009 | Kato et al. | |
| 2010/0036503 A1 | 2/2010 | Chen et al. | |
| 2010/0166894 A1 | 7/2010 | Tai | |
| 2010/0211173 A1 | 8/2010 | Bardos et al. | |
| 2010/0217268 A1 | 8/2010 | Bloebaum et al. | |
| 2010/0247651 A1 | 9/2010 | Kestler et al. | |
| 2010/0297066 A1* | 11/2010 | Stopek | A61K 9/0024 424/85.2 |
| 2011/0086008 A1 | 4/2011 | Hoemann et al. | |
| 2012/0014884 A1 | 1/2012 | Trivedi et al. | |
| 2012/0053606 A1 | 3/2012 | Schmitz et al. | |
| 2012/0107412 A1 | 5/2012 | Gammelsaeter et al. | |
| 2012/0165848 A1 | 6/2012 | Slayton | |
| 2012/0265204 A1 | 10/2012 | Schmierer et al. | |

FOREIGN PATENT DOCUMENTS

| | | |
|---|---|---|
| GB | 2093353 A | 9/1982 |
| WO | 2000002905 A2 | 1/2000 |
| WO | 2005023324 A1 | 3/2005 |
| WO | 2008086147 A1 | 7/2008 |
| WO | 2010148125 A1 | 12/2010 |
| WO | 2011089779 A1 | 7/2011 |

OTHER PUBLICATIONS

Gaertner, Wolfgang, "Frequency Dependence of Ultrasonic Cavitation," The Journal of the Acoustical Society of America, 26.6, 1954: 977-980.

Mithoefer, Kai, et al., "Chondral Resurfacing of Articular Cartilage Defects in the Knee with the Microfracture Technique," JBJS Essential Surgical Techniques, 1 suppl 2, 2006: 294-304.

O'Daly, Brendan J. et al., "High Power, Low Frequency Ultrasound: Meniscal Tissue Interaction and Ablation Characteristics," Ultrasound in Medicine & Biology, 37.4, 2011:556-567.

Spahn, et al., "Treatment of Chondral Defects by Hydro Jet," Results of a Preliminary Scanning Electron Microscopic Evaluation, Archives of Orthopaedic and Trauma Surgery, 126.4, 2006:223-227.

International Preliminary Report on Patentability dated May 21, 2015 for PCT/US2013/069123, filed on Nov. 3, 2013.

Mithoefer et al., "Chondral Resurfacing of Articular Cartilage Defects in the Knee with the Microfracture Technique, Surgical Technique," Journal of Bone and Joint Surgery, Sep. 1, 2006, vol. 8A, No. 1 (Supp. 2); pp. 294-298.

Frisbie et al., "Effects of Calcified Cartilage on Healing of Chondral Defects Treated with Microfracture in Horses," American Journal of Sports Medicine, Jul. 10, 2006, vol. 34, No. 11, p. 1825.

Gruber et al., "Induction of Interleukin-1 in Articular Cartilage by Explantation and Cutting," Arthritis and Rheumatism, Aug. 2004, vol. 50, No. 8, p. 2539.

Hunziker et al., "Removal of Proteoglycans from the Surface of Defects in Articular Cartilage Transiently Enhances overage by Repair Cells," Journal of Bone and Joint Surgery, Jan. 1998, vol. 80, No. 1, pp. 145-146.

International Search Report dated Apr. 8, 2014 for PCT/US2013/069123, filed on Nov. 8, 2013.

* cited by examiner

A

B

… (1)

METHODS AND COMPOSITIONS SUITABLE FOR IMPROVED REATTACHMENT OF DETACHED CARTILAGE TO SUBCHONDRAL BONE

BACKGROUND

Over 16 million people in the U.S. suffer from severe joint pain and related dysfunction, such as loss of motion, as a result of injury or osteoarthritis. In particular, loss of function of the knees and other joints can severely impact mobility and thus the patient's quality of life. The biological basis of joint problems is the deterioration of articular cartilage, which covers the bone at the joint surface and performs many complex functions. The deterioration of anticular cartilage is often preceded by the delamination of the cartilage. Medical intervention at the delamination stage of the disease provides an opportunity to circumvent further degradation and associated complications.

The interface between bone and cartilage is the interface between a vascularized (the bone) and mostly avascular (the cartilage) tissue as well as mineralized (ossified) and non-minerilized collagen matrices. Traumatic injury, as well as such conditions as osteoarthritis and aging, often results in damage to the articular cartilage, which may also involve damage to the underlying bone. Often, this damage manifests itself in the delamination of the cartilage from the bone. Therefore, there is a need for a method of treatment which meets the disparate needs of both tissue types and allows or encourages the healing process to progress towards restoration of both types of tissues at the same site by promoting the reattachment or relamination of the cartilage to the bone.

Prior art methods for promoting the reattachment of cartilage to the bone are not without problems. Prior art treatments include, for example, autograph procedures such as osteochondral autograph transfer system (Mosaicplasty). These procedures remove an osteochondral plug from a non-load bearing area and graft it into the defect site. However, these procedures require invasive surgical procedures and, therefore, longer recuperative times.

Arthroscopic lavage is a "cleaning up" procedure of the knee joint. This short term solution is not considered an articular cartilage repair procedure but rather a treatment to reduce pain, mechanical restriction and inflammation. Lavage focuses on removing degenerative articular cartilage flaps and fibrous tissue. The main target group is patients with very small defects of the articular cartilage. Arthroscopic debridement is a surgical technique that is effective in removing areas of loose, mechanically redundant cartilage (joint lining) and inflamed tissue (synovitis) from the joint.

Other procedures consist of injecting cartilage cells under a periosteal flap, however, the procedure lacks inter-patient consistency with some patients maintaining little relief months or years later and the surgical procedure is technically challenging and expensive. Marrow stimulating techniques including abrasion arthroscopy, subchondral bone drilling and microfracture typically result in fibrocartilage filling the defect site. In these procedures, the subchondral bone is perforated to generate a blood clot within the defect. However, marrow stimulation techniques often insufficiently fill the chondral defect and the repair material is often fibrocartilage (which is not as good mechanically as hyaline cartilage). The blood clot takes about 8 weeks to become fibrous tissue and it takes 4 months to become fibrocartilage thus needing extensive rehabilitation time. However, there is a significant possibility of the symptoms returning as the fibrocartilage wears away, forcing the patient to undergo further articular cartilage repair.

Marrow stimulation techniques have been augmented with administration of peripheral blood monocytes (PMBCs) with limited success. Microdrilling surgery creates a blood clot scaffold on which injected PBPC's can be recruited and enhance chondrogenesis at the site of the contained lesion (Saw, K Y, et al., (Epub 2011 Feb. 19). "Articular cartilage regeneration with autologous peripheral blood progenitor cells and hyaluronic Acid after arthroscopic subchondral drilling: a report of 5 cases with histology". *Arthroscopy* 27 (4):493).

Allogenic transplantation of osteochondral grafts has had clinical success, but supply is limited and has a risk of infection. This technique/repair requires transplant sections of bone and cartilage. The damaged section of bone and cartilage is removed from the joint then a new healthy dowel of bone with its cartilage covering is punched out of the same joint and replanted into the hole left from removing the old damaged bone and cartilage. The healthy bone and cartilage are taken from areas of low stress in the joint so as to prevent weakening the joint. Depending on the severity and overall size of the damage multiple plugs or dowels may be required to adequately repair the joint, which becomes difficult for osteochondral autografts and can limit its use to non-severely damaged tissue.

The prior art techniques involving removal of the delaminated cartilage is actually not in the patient's best interest because, as described above, the tissue that forms to replace the removed cartilage, called fibrocartilage, is not as robust as the original hyaline cartilage.

Other prior art techniques include the use of scaffolds or matrixes to provide a structure upon which chondrocytes may migrate and form new cartilage. For example, one such technique is provided in US Patent Application No. 2003/0114936, which describes implantable composite materials of gradated matrices for the promotion of cell growth, which is incorporated herein by reference. Other prior art references directed towards the use of scaffolds and matrices are described, infra.

Thus, because of the limitations of the prior art procedures, it has been recognized that reattachment of the hyaline cartilage is desirable. The hyaline cartilage does not readily reattach on its own—if it did treatment options would not be necessary. Prior art attempts have used adhesives, for example. However, these attempts have met with limited success. This is at least in part because even so called "biocompatible" adhesives are made from materials foreign to the patient and/or the joint. Thus, breakdown of the adhesion frequently occurs thereby only providing a temporary solution to the condition. Further, the adhesive layer creates a barrier to the cartilage cells that are necessary for reattachment of the cartilage to the underlying bone.

Thus, what is needed in the art are new compositions and procedures that provide for the successful reattachment of delaminated hyaline cartilage preferably without surgical intervention or with minimal surgical intervention.

SUMMARY OF THE INVENTION

The present invention describes compositions and methods for the reattachment of delaminated cartilage from the underlying bone. Delaminated cartilage acquires an acellular layer at the surface that is proximal to the bone surface. The major barrier to reattachment is the acellular layer. In essence, the acellular layer acts to prevent viable cells from attaching to the underlying subchondral bone. The invention is related to the novel and non-obvious discovery that removal of this acellular layer promotes reattachment of the delaminated cartilage to the surface of the subchondrial bone. It has been identified that more successful regrowth between the cartilage and subchondral bone occurs if a thin layer (approximately 0.1 mm=100 µM although the dimension may be from 0.02 mm to 1.0 mm depending on the particular circumstances entailed) of material is removed from the cartilage surface prior to reattachment. Although the inventors do not wished to be limited by theory, it is believed that removal of the acellular layer aids the reattachment of the cartilage to the subchondral bone by exposing living chondrocytes in the cartilage to the bone surface. In other words, the present inventors found that if the acellular layer is removed, reattachment of the cartilage to the bone can commence because viable cells can, for example, form attachments with the bone surface and reestablish a healthy extracellular environment. One reason why prior art biocompatible adhesives tend to fail is because they are attempting to 'glue' dead cells to healthy tissue. The removal of the acellular tissue and dead cells should be performed gently, otherwise further layers of cells may be damaged and a new acellular layer may be created. The present invention is directed towards several devices and methods of gently removing part of or all of the acellular layer of the delaminated cartilage thereby aiding in the reattachment of the delaminated cartilage to the subchondrial bone.

Methods of removal of the acellular layer of the delaminated cartilage include the use of a physiological carrier or a degradable adhesive that has been chemically or otherwise modified to initiate a mild toxicological reaction resulting in inflammation on and within the cartilage tissue. Exemplary modifications of the degradable adhesive include formulations having crystalline components suitable to induce an inflammatory reaction, the addition of materials or molecules that would cause an inflammatory reaction (e.g., cytokines, etc.) or materials or molecules that would cause direct degradation of the cartilage (e.g., enzymes such as, for example, collagenase, hyaluronidase, etc.).

Another embodiment of the invention causes degradation of the acellular layer of the delaminated cartilage by utilizing a suitable material to produce mildly toxic degradation products. An exemplary material is poly-glycolic acid (PGA). One embodiment involves placing a lattice-like (i.e., porous or non-continuous) material comprised of PGA between the delaminated cartilage and bone. Dimensions of the lattice (e.g., distance between polymer strands and thickness [diameter or area to surface ratio of a cross-section for non-circular strands] of the strands) are used to control the degradation characteristics of the material.

Both of these embodiments may include preparation of the subchondral bone bed (e.g., microfracture, Pridie drilling, etc.). Both of these embodiments may also include the administration of biocompatible adhesives.

The following prior art disclosures teach prior art compositions and methods for the treatment of damaged or delaminated cartilage and are presented here to provide contrast with the present invention and to delineate and highlight the novel and non-obvious distinctions between the present invention and the prior art. All are incorporated herein by reference.

U.S. Patent Publication No. 2009/0047322 to Vange, et al., describes biodegradable polymers comprising MPEG-PLGA (methoxypoly(ethylene glycol)-poly(lactide-co-glycolide)) for use in preparing a scaffold for use in promoting growth of fibroblasts in wound repair. The publication teaches that the invention is useful for supporting cell adhesion and/or in-growth for regeneration of tissue including cartilage and bone. In contrast, the present invention works to promote the degradation of the acellular layer of delaminated cartilage by, at least in one embodiment, promoting inflammation at the repair site.

U.S. Pat. No. 7,727,542 to DiBenedetto, et al., is related to bioactive materials made from fibroin-based solutions, suspensions and gels that can be used alone or with co-polymer particles to support the construction, repair and regeneration of bone and other tissues. In contrast to the present invention, there is no discussion of degradation of tissue or of the acellular layer of delaminated cartilage to promote reattachment of the cartilage to the bone at the cartilage-bone interface.

U.S. Pat. No. 6,784,282 Hwang, et al., (formerly U.S. Publication No. 2003/0008826) describes a method for treating cartilage with synovial fluid and poly(hydroxyl substituted amino acid). The combination creates a liquid crystalline matrix on the tissue surface resulting in modification of the cartilage surface characteristics. The cartilage surface modification of this invention is believed to improve the bonding of surgical glues. In contrast to the present invention, there is no discussion of degradation of the acellular layer of delaminated cartilage.

U.S. Patent Publication No. 2011/0086008 to Hoemann, et al., describes an invention related to the repair and regeneration of cartilage and other tissues. The invention discloses a temperature-dependent polymer gel composition that can adhere to tissue and promote support for cell proliferation. The composition may comprise polyglycolic acid (PGA) (see, abstract and paragraph [0029]). In contrast to the present invention, there is no discussion of degradation of the acellular layer of delaminated cartilage.

DETAILED DESCRIPTION OF THE INVENTION

Figure 1:
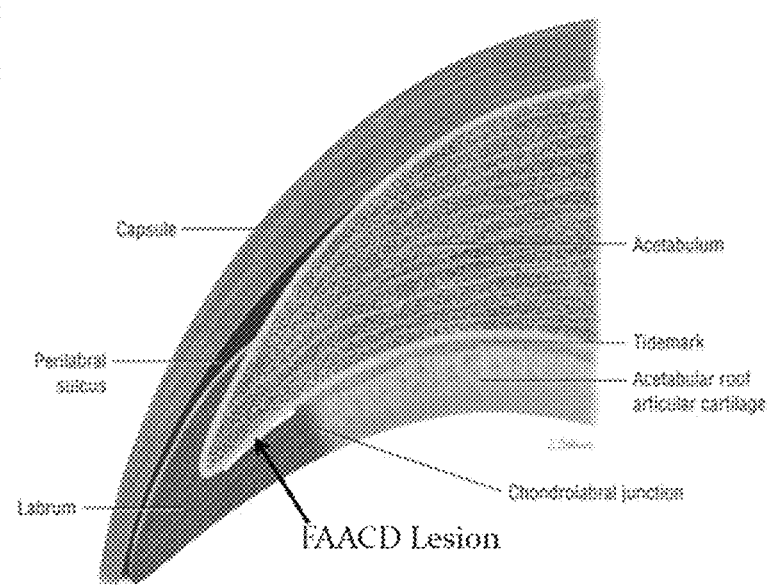
FIG. 1 shows a schematic representation of the separation of the cartilage with the underlying bone. The "tidemark," as indicated in the figure, is the cartilage-bone interface where the cartilage lining of the joints often shears off of the bone.
Figure 2:
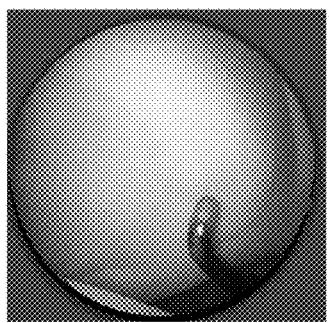
FIG. 2 (A & B) shows photographs of the progression of the shearing process. The shearing often starts as a bubble, as illustrated in the right hand photograph (A), and progresses into an open flap, as illustrated in the left hand photograph (B).
Figure 2:
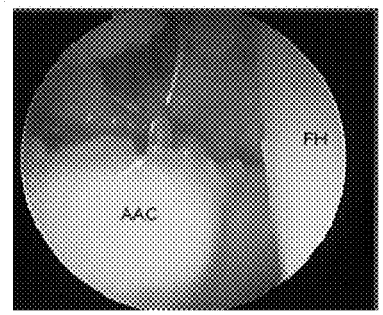
Figure 3:
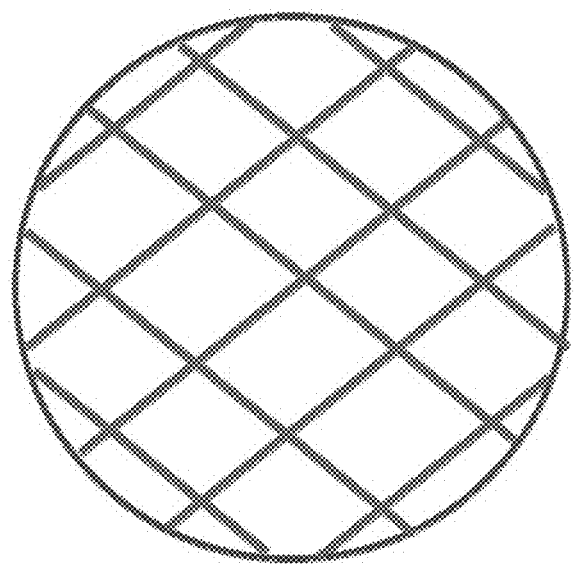
FIG. 3 shows one representation of the PGA lattice design of the present invention. The lines represent strands of material with spaces between them.

Cartilage is an avascular tissue composed of about 5-10% by weight of living cells. There are three major types of cartilage in the body: hyaline, fibrocartilage, and elastic cartilage. Hyaline cartilage covers the epiphyses of the bone and, in synovial joints, lies within a fluid filled capsule. Fibrocartilage composes the intervertebral discs separating the vertebrae of the spinal columns. Elastic cartilage is present in areas requiring extreme resilience, such as the tip of the nose. Cartilage is formed by and contains cells called chondrocytes.

Articular cartilage is composed of hyaline cartilage which has unique properties, such as viscoelastic deformation, that allow it to absorb shock, distribute loads and facilitate stable motion. Self-repair of hyaline cartilage is limited and the tissue that forms is usually a combination of hyaline and fibrocartilage, which is not as robust as the original hyaline cartilage, does not perform as well as hyaline cartilage and can degrade over time.

The extracellular matrix of hyaline cartilage contains closely packed Type II collagen fibers and proteoglycans including hyaluronate and glycoaminoglycans in a chondroitin sulfate matrix. Chondrocytes receive nutrients and dispose of wastes by diffusion through the matrix and are believed to have limited mobility or ability to divide and regenerate damaged tissue. Chondrocytes normally produce anti-angiogenesis factors. However, when large areas of cartilage are damaged, overgrowth by fibroblasts and neovascularization of the area may result in the formation of scar tissue or callus instead of articular cartilage. A subsequent ingrowth of bone forming cells may result in calcium deposition in these areas, causing further deformation of the local area.

Although attempts have been made to facilitate repair of the bone-cartilage interface in the prior art (as described above), those attempts provide the patient with a suboptimal solution to the condition often resulting in limited mobility due to stiffness and discomfort or pain. The present invention provides a greatly improved solution to the repair of delimitation of cartilage from the underlying bone thereby resulting in greatly improved patient recovery.

The prior art techniques including removal of the delaminated cartilage is actually not in the patient's best interest since the tissue that forms to replace the removed cartilage, called fibrocartilage, is not as robust as the original hyaline cartilage. Thus, it has been recognized that reattachment of the hyaline cartilage is desirable. The hyaline cartilage does not readily reattach on its own—if it did treatment options would not be necessary. Prior art attempts have used adhesives, for example. However, these attempts have met with limited success. This is at least in part because even so called "biocompatible" adhesives are made from materials foreign to the patient and/or the joint. Thus, breakdown of the adhesion frequently occurs thereby only providing only a temporary solution to the condition.

The present invention is directed towards the inventive concept that the delaminated hyaline cartilage of the patient's joint can be induced to reattach to the underlying bone with a minimally invasive procedure. The present inventors have discovered that successful regrowth between the cartilage and subchondral bone occurs if a thin layer of material is removed from the cartilage surface (the surface facing the bone) prior to joining.

Numerous compositions and methods can be used to promote the removal of the thin layer of cartilage material. For example, such agents can be selected that induce or initiate a mild toxicological reaction resulting in inflammation or mild digestion within the cartilage tissue or on the surface of the cartilage tissue. The agents would preferably be administered in a carrier, more preferably in a biocompatible and/or biodegradable carrier, examples of which are known to those of ordinary skill in the art. In some embodiments, the carrier may be a biocompatible adhesive. The biocompatible adhesive may also be biodegradable, for example, over a period of days or weeks. The carrier/adhesive would aid in the reattachment of the cartilage to the underlying bone in that it would help the cartilage maintain proximity to the bone while the growth and physiological reattachment of the cartilage is promoted by the compositions and methods of the present invention. Fibrin-based adhesives (e.g., fibrin glues) are a non-limiting example of a suitable carrier/adhesive.

As is known in the art, fibrin glue (also called fibrin sealant), consists of two main components: fibrinogen and thrombin. These are typically, for example, loaded into two syringes with tips forming a common port. When injected, the two components meet in equal volumes at the point of delivery. The thrombin converts the fibrinogen to fibrin by enzymatic action at a rate determined by the concentration of thrombin. The more concentrated thrombin solution produces a fibrin clot in about 10 seconds, and the more dilute thrombin solution forms the clot about 60 seconds after the glue is applied to the surgical field. Both the extrinsic and the intrinsic mechanisms of blood coagulation are bypassed, but the physiological final common pathway of coagulation is faithfully replicated. Factor XIII (present in the fibrinogen component of the glue) cross links and stabilizes the clot's fibrin monomers. Some preparations of fibrin glue contain aprotinin to delay the fibrinolytic action of plasmin. (Fibrin Glue, BMJ, 9 Apr. 1994:308:933). Fibrin glue is used as a tissue adhesive. This glue can be used for repairing dura tears, bronchial fistulas and for achieving hemostasis after spleen and liver trauma.

Non-limiting examples of such agents (with or without a carrier) that can be used in the compositions and methods of the present invention and introduced to the afflicted area and that can digest or inflame the surface of the cartilage include agents such as crystalline substances (for example, substances similar to or chemically related to depo-corticosteroids). The action of the crystalline agent invokes an inflammatory reaction and thereby promotes a degradative response to the cartilage tissue surface.

In another embodiment, the agent to be introduced into the afflicted area can be cytokines that are known to promote an inflammatory reaction. Suitable inflammatory cytokines are known to those or ordinary skill in the art and can be readily identified in view of the teachings of the present specification and including, but not limited to, TNF, IL-1 and IL-6. Such agents would naturally degrade over time.

In yet another embodiment, the agent is selected from compounds known to digest cartilage to at least some degree. Non-limiting examples of such agents include collagenase and hyaluronidase, etc. Other suitable agents are known to those of ordinary skill in the art and can be readily identified in view of the teachings of the present specification. Such agents would naturally degrade over time.

Exfoliation is another method contemplated by and compatible with the present invention for use in the reattachment of delaminated cartilage from the underlying bone. An exfoliant is used to slough away (e.g., gently slough away) dead cells and tissues that are still adhered to viable, healthy cells and cell layers. Exfoliants are often used for dermal applications to remove dead cells and allow a better transfer of a skin care product to the healthy skin. The same concept has been adapted herein for cartilage repair. To enable the transfer of live cells for integration, the dead cells and associated tissue is removed gently. Contemplated exfoliants suitable for use in the present invention include, but are not limited to, mechanical exfoliants such as granules (or other mild abrasive) to "scrub" or otherwise remove away the dead cartilage cells. Some non-limiting examples of mechanical exfoliants contemplated by the present invention are sodium tetraborate decahydrate granules, polyethylene silica, calcium carbonate, natural ground seed or beans, aluminum oxide, monosaccharides, disaccharides, ice crystals, etc. Also contemplated by the present invention are chemical exfoliants such as, but not limited to, alpha hydroxyl acid, citrus juices, beta hydroxyl acid and papain, a natural digestive enzyme found in papya.

In some embodiments of the present invention it is contemplated that the bone surface is to be prepared in addition to the surface of the cartilage. The methods suitable to prepare the bone surface include, but are not limited to, the removal of any calcified cartilage that is adhered to the bone. The depth of the tissue removal is contemplated to be between 0.1 mm and 3.0 mm. Additionally, subchondral disruption methods such as microfracture, Pridie drilling (named after Kenneth Pridie, a British athlete and orthopedic surgeon: Pridie is known for a particular cartilage repair technique where repair by fibrocartilage formation is stimulated by drilling small holes into the subchondral bone plate after surgical debridement of cartilage defects, known as the Pridie Drilling), etc., could be performed in combination with any embodiment of the present invention.

Administration of the compositions of the present invention may be performed by any suitable method known to those of ordinary skill in the art. Such techniques include, but are not limited to, injection and administration though endoscopic or surgical access ports. If desired, the administration of the compositions of the present invention may be made while observing the procedure through any of the visual imaging techniques known to those of skill in the art such as ultrasound, x-ray and magnetic imaging. Although not strictly necessary, visualization of the administration of the compositions of the present invention may allow the practitioner to be more precise in directing the composition to the desired location(s). Techniques involving mechanical disruption, for example, to prepare the bone surface by microfracture or Pridie drilling, surgical access may be necessary.

In the context of the present invention the term "acellular cartilage layer" (and similar) refers to the layer of cartilage where few or no living (viable) chondrocytes are present at or in close proximity to the delaminated surface of the cartilage or directly exposed to the outer surface or proximal environment of the delaminated surface of the cartilage. The acellular layer typically has from 10% to 100% fewer living (viable) cells than the "cellular" region of the cartilage. The acellular layer typically extends from 0.02 mm to 1.0 mm from the delaminated surface of the cartilage.

The present invention will now be described in the context of several specific examples. It is to be understood that the present invention is by no means limited to the particular compositions and methods herein described and/or shown in the drawings, but also comprises any modifications or equivalents within the scope if the invention.

EXEMPLIFICATION

Example 1

In this example subjects having delaminated cartilage will be treated with either 1) a fibrin-based adhesive, 2) a fibrin-based adhesive comprising an agent suitable for the removal of at least a portion of the acellular layer of the delaminated cartilage, 3) an agent suitable for the removal of at least a portion of the acellular layer of the delaminated cartilage in a physiologically compatible, non-inflammation producing, non-adhesive carrier solution such as sterile saline or, 4) treated with a placebo (e.g., carrier substance used in the test conditions 1 and 2 related above or a physiologically compatible, non-inflammation producing solution such as sterile saline). The carrier substances used in conditions 3) and 4) above will be of the same viscosity, pH, etc., as the fibrin-based adhesive compositions. The subjects may be suitable animal models or human patients participating in a clinical trial. Pigs and rabbits (Ebihara G, et al., Cartilage repair in transplanted scaffold-free chondrocyte sheets using a minipig model, Biomaterials. 2012 May; 33(15):3846-51. Epub 2012 Feb. 25), goats (Vasara A I, et al., Subchondral bone reaction associated with chondral defect and attempted cartilage repair in goats, Calcif Tissue Int. 2004 January; 74(1):107-14. Epub 2003 Oct. 20) and rats (Mogan, C., et al., Application of in vivo micro-computed tomography in the temporal characterisation of subchondral bone architecture in a rat model of low-dose monosodium iodoacetate-induced osteoarthritis, Arthritis Res Ther. 2011; 13(6):R210. Epub 2011 Dec. 21) are known in the art as being a suitable model system for the study of bone, cartilage and other joint-related diseases in humans, however, any mammalian model system known to one of ordinary skill in the art for studying the delamination of cartilage can be used.

The reattachment of the cartilage will be monitored by methods known to those of skill in the art. Such methods may include, for example, x-rays, magnetic imaging, ultrasound imaging, CT scanning, etc., of the treated area. Monitoring will take place as long as necessary to gather long term results. For example, monitoring may take place weekly for up to three months and then monthly or quarterly for up to five years or more. The results will show a statistically significant improvement of reattachment with conditions 2) and 3) as compared to conditions 1) and 4). Condition 4) will show the poorest performance. Long term monitoring of the subjects will take into account use of the joint by the subject or other location treated by the conditions noted above.

One of ordinary skill in the art will be able to develop other experiments to quantitate specific agents used in the present invention as well as optimal concentrations, doses, booster doses, etc., and to determine a system of pretreatment that includes preparation of the bone surface and/or mechanical disruption using, for example, Pridle drilling, etc.

The invention claimed is:

1. A method for promoting the reattachment of a delaminated cartilage to a subchondral bone at a cartilage-bone interface comprising:
    contacting an acellular layer at a surface on the delaminated cartilage that is proximal to the bone surface with one or more agents contained within a biocompatible adhesive, where the one or more agents are in an amount effective to promote a controlled degradation of the acellular cartilage layer, thereby promoting conditions for the reattachment of said delaminated cartilage to the surface of said subchondral bone, wherein said one or more agents are selected from the group consisting of cytokines, enzymes, and a lattice comprised of polyglycolic acid.

2. The method of claim 1, wherein said method additionally comprises a subchondral disruption of the bone surface.

3. The method of claim 1, wherein said method additionally comprises at least partial removal of a calcified cartilage from the bone surface.

4. The method of claim 2, wherein said subchondral disruption of the bone surface removes from approximately 0.02 mm to approximately 3.0 mm of tissue from the surface.

5. The method of claim 1, wherein said controlled degradation of said acellular layer comprises promoting an inflammatory reaction.

6. The method of claim 1, wherein said biocompatible adhesive is a fibrin-based adhesive.

7. The method of claim 1, wherein the controlled degradation of said acellular layer comprises removing approximately 0.02 mm to approximately 1.0 mm of the cartilage.

8. The method of claim 7, wherein the controlled degradation of said acellular layer comprises removing approximately 0.1 mm of the cartilage.

9. The method of claim 1, wherein said cytokines are selected from the group consisting of tumor necrosis factor (TNF), Interleukin-1 (IL-1) and interleukin-6 (IL-6).

10. The method of claim 1, wherein the acellular layer is also contacted with a crystalline compound comprising a depo-corticosteroid.

\* \* \* \* \*